United States Patent
Sugaya et al.

(10) Patent No.: US 7,470,368 B2
(45) Date of Patent: Dec. 30, 2008

(54) HYDROPHILIC SUBSTANCE AND A PRODUCTION METHOD THEREOF

(75) Inventors: Hiroyuki Sugaya, Otsu (JP); Yoshihiro Eika, Otsu (JP); Yoshiyuki Ueno, Otsu (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 11/907,655

(22) Filed: Oct. 16, 2007

(65) Prior Publication Data

US 2008/0061002 A1 Mar. 13, 2008

Related U.S. Application Data

(62) Division of application No. 10/490,312, filed as application No. PCT/JP02/10320 on Oct. 3, 2002, now abandoned.

(30) Foreign Application Priority Data

Oct. 4, 2001 (JP) .............................. 2001-308677

(51) Int. Cl.
*B01D 11/00* (2006.01)
*B01D 61/00* (2006.01)
*B01D 63/00* (2006.01)

(52) U.S. Cl. ............. 210/645; 210/500.37; 210/500.41; 210/500.42; 210/321.71

(58) Field of Classification Search ................. 210/645, 210/500.27, 500.41, 490, 500.37, 500.42, 210/500.23, 502.1, 663, 321.71; 604/8
See application file for complete search history.

(56) References Cited

U.S. PATENT DOCUMENTS

| 5,004,543 | A | 4/1991 | Pluskal et al. |
| 5,079,272 | A | 1/1992 | Allegrezza et al. |
| 5,489,303 | A | 2/1996 | Sasaki et al. |
| 5,762,798 | A | 6/1998 | Wenthold et al. |
| 6,010,475 | A | 1/2000 | Thomas et al. |
| 6,045,694 | A * | 4/2000 | Wang et al. ............. 210/500.37 |
| 6,168,718 | B1 | 1/2001 | Sutter et al. |
| 6,177,013 | B1 | 1/2001 | Thomas et al. |
| 6,193,891 | B1 * | 2/2001 | Kent et al. .................. 210/645 |
| 6,248,238 | B1 * | 6/2001 | Burtin et al. ................. 210/646 |
| 6,355,730 | B1 | 3/2002 | Kozawa et al. |
| 6,409,024 | B1 * | 6/2002 | Nakashima et al. ......... 210/456 |
| 6,423,024 | B1 * | 7/2002 | Strom et al. .................... 604/8 |
| 6,432,309 | B1 | 8/2002 | Fuke et al. |
| 6,478,960 | B1 * | 11/2002 | Saruhashi et al. ...... 210/500.23 |
| 6,605,218 | B2 | 8/2003 | Kozawa et al. |
| 6,632,361 | B2 | 10/2003 | Niklas et al. |
| 6,945,257 | B2 | 9/2005 | Tabani et al. |
| 6,960,297 | B2 | 11/2005 | Kozawa et al. |
| 2005/0273031 | A1 | 12/2005 | Ueno et al. |

FOREIGN PATENT DOCUMENTS

| CN | 1257434 A | 6/2000 |
| EP | 1 121 972 A | 8/2001 |
| JP | 53-134876 | 11/1978 |
| JP | 63-97634 | 4/1988 |
| JP | 10-168193 | 6/1988 |
| JP | 2000-254222 | 9/2000 |
| JP | 2002-28461 | 1/2002 |
| JP | 2002-102339 | 4/2002 |
| JP | 2002-102692 | 4/2002 |

OTHER PUBLICATIONS

Gambro. Renal Products, Polyflux L, Highest hemocompactibility with lowest TCC generation, Willey and Sons, Inc. 199-2005, http://www3.interscience.willey.com/cgi-bin/astract/109867309/ABSTRACT.

* cited by examiner

*Primary Examiner*—Ana M Fortuna
(74) *Attorney, Agent, or Firm*—Nixon & Vanderhye P.C.

(57) ABSTRACT

The present invention relates to a hydrophilic substance production method characterized in that polyvinylpyrrolidone-containing material wetted with an aqueous solution of a cationic polymer is treated with radiation. The invention makes it possible to produce material for blood treatment that prevents adsorption of blood platelets.

8 Claims, No Drawings

HYDROPHILIC SUBSTANCE AND A PRODUCTION METHOD THEREOF

This application is a division of application Ser. No. 10/490,312, filed Mar. 19, 2004, now abandoned which in turn is a US national phase of international application PCT/JP02/10320 filed in Japanese on 3 Oct. 2002, which designated the US. PCT/JP02/10320 claims priority to Japanese Application No. 2001-308677 filed 4 Oct. 2001, the entire content of which is hereby incorporated by reference in this application.

BACKGROUND ART

The present invention relates to a hydrophilic substance and a production method thereof, particularly to a hydrophilic substance with resistance to adsorption of blood platelets, and a production method thereof. Consisting of a cationic polymer component, it is suited to uses that take advantage of good features of a cationic polymer.

PRIOR ART

A variety of polymer materials are presently used in the medical field. When used in artificial blood vessels, catheters, artificial kidneys, or other products that directly contact with blood, serious problems can arise with adhesion of blood components, such as plasma protein and blood platelets, and resultant formation of blood clots. A separation membrane used for blood purification, for example, may suffer problems with blood residue on the membrane that results from the activation of blood platelets. To avoid such blood residue, hydrophilic substances that do not adsorb blood platelets significantly have been strongly sought for.

Conventional materials for blood purification include various polymers such as cellulose, cellulose acetate, cellulose triacetate, polyolefin, polyimide, polycarbonate, polyallylate, polyester, polyacrylonitrile, polymethyl methacrylate, polyamide, and polysulfone. In particular, polysulfones, with high heat resistance, have been used as material for dialysis membrane and other different products including separate membranes and films. When used as material for blood purification, they are blended with a hydrophilic polymer, such as polyvinylpyrrolidone, to improve their compatibility with blood.

OBJECTIVE OF THE INVENTION

Blending with a hydrophilic polymer, such as polyvinylpyrrolidone, alone is not significantly effective in controlling the activation of blood platelets. The present invention aims to eliminate the defect of conventional materials to provide a method to produce a hydrophilic substance that does not suffer heavy adhesion of blood platelets.

DISCLOSURE OF THE INVENTION

To solve the above problem, the present invention has the following features. Specifically, the invention relates to a hydrophilic substance production method characterized by irradiation of a polyvinylpyrrolidone-containing material wetted with an aqueous solution of a cationic polymer, and also relates to a hydrophilic substance consisting of a polyvinylpyrrolidone-containing material and a cationic polymer.

BEST MODE FOR CARRYING OUT THE INVENTION

The weight average molecular weight of a polyvinylpyrrolidone material to be used for the invention is not limited to a particular range, but should preferably be 2,000 to 2,000,000, more preferably 10,000 to 1,500,000. High in availability, commercial products with a weight average molecular weight of 1,100,000, 45,000, 29,000, 9,000, or 29,000 have been used preferably. A polyvinylpyrrolidone product should have such a weight average molecular weight as cited above at the time of feeding to the production process. If such a procedure as radiation-induced crosslinking is performed, the polyvinylpyrrolidone component of the resulting hydrophilic substance may have a larger molecular weight than at the time of feeding.

Commercial polyvinylpyrrolidone products include Kollidon 12 PF, 17 PF, 25, 30, and 90 (supplied by BASF), Luviskol K 17, K 30, K 80, and K 90 (supplied by BASF), and Plasdone K-29/32, K-25, K-90, K-90D, and K-90M (supplied by ISP).

A polyvinylpyrrolidone product used for the invention should preferably be a homopolymer, but may be a copolymer produced by combining it with other monomers unless it degrades the good features of the present invention. The content of said other monomers in the copolymer is not limited to a particular range, but should preferably be 80 wt % or less.

Commercial polyvinylpyrrolidone copolymer products include Kollidon VA 64 (supplied by BASF), Luviskol VA 64 (supplied by BASF), Luvitec VPI55 K18P, VPI55, K72W, Quat 73W, VPMA 91W, and VPC 55 K65W (supplied by BASF), and Plasdone S-630 (supplied by ISP).

The hydrophilic substance of the present invention contains a polyvinylpyrrolidone component, but a base material should preferably be used in combination with the polyvinylpyrrolidone in order to maintain the polyvinylpyrrolidone in a stable form and to prevent it from being easily eluted, deformed, or degraded. The structure and the combining method used for the polyvinylpyrrolidone and said base material are not limited to particular ones. The base material and polyvinylpyrrolidone may be laminated, but should preferably be in a mixed or compatible form.

The base material is not limited to particular substances, but should preferably be an organic polymer. Preferred organic polymers include polysulfones.

The content of the polyvinylpyrrolidone component in hydrophilic substance of the present invention is not limited to a particular range, but should preferably be in the range from 1 wt % to 50 wt %, more preferably from 1 wt % to 10 t %, considering that the base material needs to have a certain level of strength in most cases. An appropriate content may be determined by NMR and other methods used solely or in combination.

Preferred polysulfones to be used as material for the hydrophilic substance of the present invention include, but not limited to, those having an aromatic ring, sulfonyl group, or ether group in their backbone, such as those polysulfones represented by Chemical Formula 1 or 2, where n denotes an integer that shows the degree of polymerization and should preferably be in the range of 50 to 80.

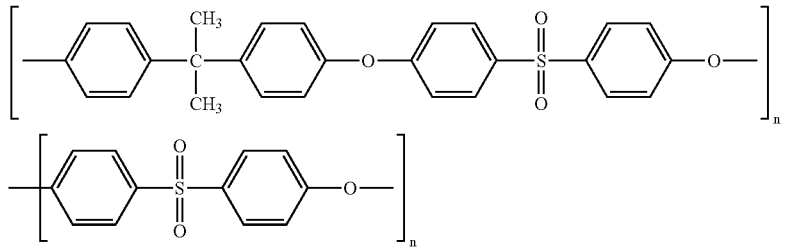

Commercial polysulfone products include Udel P-1700 and P-3500 (supplied by Teijin Amoco Engineering Plastics Limited), Ultrason S3010 and S6010 (supplied by BASF), Victrex (supplied by Sumitomo Chemical Co., Ltd.), Radel A-200A, A-300, R-5000 and R-5800 (supplied by Teijin Amoco Engineering Plastics Limited), Ultrason E (supplied by BASF), and Sumikaexcel (supplied by Sumitomo Chemical Co., Ltd.).

Polysulfone used for the invention should preferably be a polymer that comprises only those monomers which are represented by above-mentioned Chemical Formula 1 or 2, but may be a copolymer produced by combining it with other monomers unless it degrades the good features of the present invention. The content of said other monomers used to produce a copolymer is not limited to a particular range, but should preferably be 10 wt % or less.

In addition to said polyvinylpyrrolidone and base material (such as polysulfone), the hydrophilic substance of the invention may contain other polymers and additives unless it degrades the good features of the present invention. The content of such polymers and additives other than said polyvinylpyrrolidone and base material is not limited to a particular range, but should preferably be 10 wt % or less.

The hydrophilic substance of the invention is not limited to particular forms, and may be used in the form of a tube, bead, fabric, nonwoven fabric, cut fiber, flat membrane, or hollow fiber membrane. Said hydrophilic substance may also be molded into a specific form after being dissolved in a solvent, or may be used as coatings. Hollow fiber membrane, however, is preferred considering that said substance may be used to perform the function of an artificial kidney and should have a large surface area for contact with blood to achieve a high processing efficiency.

If the hydrophilic substance of the present invention is used as separation membrane, its thickness should preferably be in the range of 10 µm to 80 µm, more preferably 20 µm to 50 µm. The pore size of said membrane should preferably be 0.5% or more, more preferably 1% or more, in terms of 1% albumin permeability. If it is used in the form of hollow fiber membrane, its inner diameter should preferably be in the range of 100 µm to 300 µm, more preferably 150 µm to 200 µm.

If it is used as hollow fiber membrane, it may be produced by a conventional method. Preferred methods include a separation membrane production process in which a solution prepared by admixing and dissolving polyvinylpyrrolidone in a polysulfone-based polymer using a solvent is employed as feedstock for membrane production.

The weight ratio of said polysulfone and polyvinylpyrrolidone should preferably be in the range of 20:1 to 1:5, more preferably 5:1 to 1:1.

Preferred solvents to be used for admixing and dissolving polyvinylpyrrolidone in polysulfone include N,N-dimethylacetamide, dimethylsulfoxide, dimethylformamide, N-methylpyrrolidone, and dioxane. The content of said polysulfone-based polymer should preferably be in the range of 10 wt % to 30 wt %, more preferably 15 wt % to 25 wt %.

Production of a membrane from said feedstock is not limited to particular methods, and any known method can be used. A useful method is to discharge said feedstock from a double-annular nozzle with a liquid being injected into the inside, allow the product to run through a dry step, and then feed it to a solidification bath. In doing this, as the humidity in the dry step can have significant influence, excessive densification likely to be caused by drying in the neighborhood of the outer surface may be prevented by supplying water through the outer surface of the membrane while it is running through the dry step, in order to provide a product that is low in permeability and diffusion resistance when used for dialysis. If the relative humidity is too high, however, water would act to form a dense layer on the outer surface, which will result in a product that is high in permeability and diffusion resistance when used for dialysis. To avoid this, the relative humidity in the dry step should preferably be in the range of 60% to 90%. To suit the process, the liquid to be injected should preferably consist mainly of the solvent that is used to prepare the feedstock. When dimethylacetamide is used, for instance, the liquid to be injected should preferably be an aqueous solution of 45 wt % to 80 wt %, more preferably 60 wt % to 75 wt %.

Said cationic polymer is not limited to particular types, but should preferably be a nitrogen-containing polymer, such as one containing an amino, imino or amido group, which may have one or more selected from the group of primary, secondary or tertiary amino groups and quaternary ammonium salts. Copolymers consisting of feedstock components of these polymers and copolymers consisting of nonionic or anionic substances may also be preferred. Said cationic polymer may be linear, branched or cyclic. Its molecular weight should preferably be in the range of 600 to 10,000,000.

Typical polymers containing an amino group include polyalkyleneimine, polyallylamine, polyvinylamine, dialkylaminoalkyl dextran, chitosan, polyornithine, and polylysine, as well as those polymers produced by introducing a substituent thereinto, and copolymers consisting of monomer units thereof.

Linear or branched polyethyleneimines with a molecular weight of 600 to 10,000,000 are preferred.

Suitable polyethyleneimine derivatives may be produced by alkylation, arboxylation, phenylation, phosphorylation, or sulfonation of a polyethyleneimine up to a desired degree.

Such cationic polymers as branched polyethyleneimines and dialkylaminoethyl dextrans are preferred because of their low toxicity, high availability and easy handling.

A polyvinylpyrrolidone-containing material and a cationic polymer are integral parts of the invention, and it is necessary for both of them not to be in a significantly water-soluble form. Such a state of not being significantly water-soluble, or a water-insoluble state, is defined as a state where the solubility of these hydrophilic substances in water is 1% or less. Solid material will be obtained if a hydrophilic substance is immersed in a 9-fold weight of 37° C. water for one hour and then pulled out with tweezers or other tools, followed by vacuum drying below 50° C. Said solubility represents the ratio of the weight of this solid material to the weight of the original hydrophilic substance before immersion. If the solubility is not sufficiently low, the final product would suffer significant elution during practical use, possibly resulting in a safety hazard. To make both insoluble, they may be kneaded with a water-insoluble base material at a molecular level, or they may be treated with heat or radiation energy after being molded into a certain form. In particular, treatment with radiation is preferred because polyvinylpyrrolidone is easily crosslinked.

In said solution that contains a cationic polymer to be used to wet a polyvinylpyrrolidone-containing material, said polymer should preferably have a content of 0.01 wt % or more, more preferably 0.05 wt % or more, still more preferably 0.1 wt % or more, in order to provide a product that does not adsorb blood platelets significantly.

Said radiation treatment can work to crosslink the polyvinylpyrrolidone component in the material though the mechanism is not clearly known. Said radiation treatment is not limited to particular methods, but may be carried out by irradiating the polyvinylpyrrolidone component blended in the material, or by coating the entirety or part of the surface of molded polysulfone with polyvinylpyrrolidone or a vinylpyrrolidone monomer, followed by irradiation of said polyvinylpyrrolidone to combine it with the polysulfone base. Radiation treatment may be performed by applying gamma or electron rays to polyvinylpyrrolidone-containing material wetted with a solution of a cationic polymer.

Thus, irradiating polyvinylpyrrolidone-containing material wetted with a solution of a cationic polymer is thought to act to introduce said cationic polymer into said polyvinylpyrrolidone-containing material. Preventing excessive crosslinking from taking place in said polyvinylpyrrolidone while maintaining the hydrophilic properties of said polyvinylpyrrolidone results in low adhesiveness to blood platelets.

Said wetted state referred to herein is defined as a condition where said polyvinylpyrrolidone-containing material is immersed in said solution, or in a non-dry state after removing the solution in which said polyvinylpyrrolidone-containing material has been immersed. In such a state, therefore, said polyvinylpyrrolidone-containing material contains water. The degree of said wetting is not limited to a particular range, but in most cases said polyvinylpyrrolidone-containing material should preferably contain 1 wt % or more water relative to the weight of said material. Or, said polyvinylpyrrolidone-containing material may be immersed in said aqueous solution. The absorbed radiation dose in said wetted state should preferably be about 10-50 kGy, and sterilization may be performed simultaneously if the material is irradiated up to a dose above 20 kGy. In this case, the absorbed dose may be determined by using a dosimetric label stuck to the surface of the module.

If the sterilization dose is insufficient, steam sterilization or other such treatment may be carried out after radiation treatment of polyvinylpyrrolidone.

Treatment of polyvinylpyrrolidone would be insufficient if the dose is less than 10 kGy. On the other hand, the polysulfone base, case, and other parts may suffer significant degradation if the dose exceeds 50 kGy.

Hydrophilic material produced by the production method of the present invention can serve effectively for blood purification.

The testing method used to determine the adsorption of blood platelets by hydrophilic material of the invention in the form of hollow fiber membranes is described below.

First, 30 hollow fiber membranes are combined, and both ends of the bundle are fixed to a glass tube module case with an epoxy-based potting agent in a way that does not block the hollow portion of the hollow fiber membranes to produce a mini-module. Said mini-module is about 7 mm in diameter and about 10 cm in length. The blood inlet of the mini-module and the dialysate outlet are connected with a silicone tube, and 100 ml of distilled water is fed to the blood outlet at a flow rate of 10 ml/min to wash the inside walls of the hollow fiber membranes and the module, followed by filling them with physiological saline and closing the dialysate inlet and outlet with a cap. Then, the hollow fiber membranes are washed with physiological saline for two hours at a flow rate of 0.59 ml/min, followed by perfusing with 7 ml of a blood sample prepared by mixing 3.2% tri-sodium citrate dihydrate and fresh rabbit blood at a volume ratio of 1:9 for one hour at a flow rate of 0.59 ml/min. Then, washing is carried out with physiological saline using a 10 ml syringe, and the hollow fiber membrane side portion and the dialysate side portion are filled with 3% glutaraldehyde solution, which are left to stand overnight or more to ensure fixation with glutaraldehyde. After this, glutaraldehyde is washed away with distilled water, and the hollow fiber membranes are cut out from the mini-module, followed by vacuum drying for five hours. Part of the hollow fiber membranes is fixed with a double sided adhesive tape on the specimen table of a scanning electron microscope, and cut in the length direction to expose the inner surface. Then, sputtering is performed to form a thin Pt—Pd layer on the specimen. The inner surface of the hollow fiber membrane specimen is observed with a scanning electron microscope (S800 supplied by Hitachi, Ltd.) at a magnification ratio of 3,000, and the number of blood platelets found in an area of $1.0 \times 10^3$ $\mu m^2$ is counted. A better separating membrane has a less number of adsorbed blood platelets.

The testing method used to determine the adsorption of blood platelets by hydrophilic material, of the invention in the form of film is described below.

Molded film in the form of a sheet is placed on the bottom of a cylindrical polystyrene tube with a diameter of 18 mm, and the tube is filled with physiological saline. A blood sample prepared by mixing 3.2% tri-sodium citrate dihydrate and fresh rabbit blood at a volume ratio of 1:9 is subjected to centrifugal separation for 10 min at 1,000 rpm, and the supernatant is taken out (referred to as plasma 1). Then, the blood left after removing the supernatant is further subjected to centrifugal separation for another 10 min at 3,000 rpm, and the supernatant is taken out (referred to as plasma 2). Plasma 1 is diluted by adding plasma 2 (plasma 2 is lower in blood platelet content than plasma 1) to provide platelet-rich plasma (PRP) with a blood platelet content of $20 \times 10^6$/ml. After removing the physiological saline from the tube prepared above, 1.0 ml of said PRP is put in the tube, which is then shaken at 37° C. for one hour. After this, the specimen is washed three times with physiological saline, and the blood content is fixed with a 3% glutaraldehyde solution, followed by washing with distilled water and vacuum drying for five hours. The film is fixed with a double sided adhesive tape on the specimen table of a scanning electron microscope, and sputtering is performed to form a thin Pt—Pd layer on the specimen. The surface of the specimen is observed with a Hitachi S800 scanning electron microscope (mainly the central part of the film is observed at a magnification ratio of 3,000, because blood tends to gather in the portions of the film in contact with the tube). The number of blood platelets found in an area of $1.0 \times 10^3$ $\mu m^2$ is counted.

The hydrophilic substance produced according to the invention is highly compatible with blood. In addition, as a cationic polymer is contained, adsorptivity to lipid peroxide or endotoxin can be imparted to the hydrophilic substance. The adsorptivity to lipid peroxide (oxidized LDL) is evaluated as follows.

(1) Preparation of Antioxidized LDL Antibody

Antioxidized LDL antibody specimens prepared by Itabe et al. (H. Itabe et al., J. Biol. Chem. 269; 15274, 1994) were used. Specifically a human atherosclerotic lesion homogenate was injected to mice to immunize them, and hybridomas were prepared from the spleen of the mice, followed by selecting those which react with LDL that had been treated with copper sulfate. Their antibody was classified as mouse IgM, and they did not react with untreated LDL, acetyl LDL, or malondialdehyde LDL. They reacted with peroxides of some phosphatidylcholines, including aldehydes and hydroperoxides of phosphatidylcholines. Here, specimens were prepared by dissolving them in a 10 mM boric acid buffer solution (pH8.5) containing 150 mM NaCl (protein content 0.60 mg/ml).

(2) Preparation of Oxidized LDL

A commercial LDL product (supplied by Funakoshi Co., Ltd.) was demineralized, diluted with a phosphate buffer solution (hereafter referred to as PBS) down to a concentration of 0.2 mg/ml, and after addition of 0.5 mM copper sulfate solution up to 1 wt %, allowed to react at 37° C. for 16 hours. Oxidized LDL specimens were prepared by adding 25 mM ethylenediamine tetra-acetic acid (hereafter referred to as EDTA) up to 1 wt % and 10 wt % sodium azide up to 0.02 wt %.

(3) Procedure for Adsorption

An oxidized LDL specimen as prepared above was added to blood plasma of a normal healthy human (30-year old Japanese).

From hollow fiber membranes with an inner diameter of 200 μm and a thickness of 40 μm, a 12 cm-long mini-module consisting of 70 membranes (inner surface area 53 $cm^2$) was produced, and connected to a 2 cm-long silicone tube with an inner diameter of 7 mm (outer diameter 10 mm, product name ARAM) and a silicone tube with an inner diameter of 0.8 mm (outer diameter 1 mm, product name ARAM, a 37 cm-long tube at both ends) via an asymmetric connector, followed by perfusing with 1.5 ml of said blood plasma at 25° C. which was passed through the hollow fiber membranes for four hours at a flow rate of 0.5 ml/min (plasma supply rate was $8 \times 10^2$ ml per $m^2$ of hollow fiber membrane's inner surface).

The same perfusing procedure was performed for the silicones tubes alone without using the mini-module.

The contents of oxidized LDL, LDL and HDL in the blood plasma were determined before and after the perfusing procedure, and the adsorptive removal rate was calculated by the following equation. adsorptive removal rate (%)=rate of adsorptive removal in mini-module (%)−rate of adsorptive removal in silicone tubes (%) adsorptive removal rate (%) of each portion=100×(content before perfusing−content after perfusing)/content before perfusing (4) Determination of Oxidized LDL Content An antioxidized LDL antibody was diluted with PBS, dispensed to a 96-well plate at a rate of 100 μl/well, and after shaking at room temperature for two hours, allowed to stand at 4° C. overnight or more to ensure adsorption on the walls.

The antibody solution was removed out of the wells, and a Tris-hydrochloric acid buffer solution (pH8.0) containing 1 wt % bovine serum albumin (BSA Fraction V supplied by Seikagaku Corporation) was dispensed at a rate of 200 μl/well, followed by shaking at room temperature for two hours to block the walls. After removing the BSA solution out of the wells, said plasma containing oxidized LDL and a standard liquid for calibration curve plotting (PBS buffer containing 0-2 μg/ml oxidized LDL) were dispensed at a rate of 100 μm/well. Then, the specimens were shaken at room temperature for 30 min and allowed to stand overnight at 4° C.

After allowing the specimens to come to room temperature, the solution was removed out of the wells, and the wells were washed three times with a Tris-hydrochloric acid buffer solution (pH8.0) containing 0.05 wt % Tween 20 (supplied by Katayama Chemical, Inc.). Then, 100 ml of sheep anti-apoB antibody (the bindind site) diluted with a 2,000-fold volume of PBS was put in each washed well, and shaken at room temperature for two hours, and after removing the sheep anti-apoB antibody out of the wells, the wells were washed three times with a Tris-hydrochloric acid buffer solution (pH8.0) containing 0.05 wt % Tween 20. Then, 100 ml of alkaline phosphatase labeled donky anti-sheep IgG antibody (Chemicon) diluted with a 2,000-fold volume of a Tris-hydrochloric acid buffer solution (pH8.0) containing 2 wt % Blockace (supplied by Dainippon Pharmaceutical Co., Ltd.) was put in each well, and shaken at room temperature for two hours. Subsequently, after removing the labeled antibody out of the wells, the wells were washed three times with a Tris-hydrochloric acid buffer solution (pH8.0) containing 0.05 wt % Tween 20 and two times with a Tris-hydrochloric acid buffer solution (pH8.0). Then, 100 μl of a 1 mg/ml solution (0.0005M $MgCl_2$, 1M diethanolamine buffer solution, pH9.8) of p-nitrophenylphosphoric acid (supplied by Boehringer Mannheim GmbH) was put in each well, and allowed to react at room temperature for an appropriate period of time, followed by determining the 415 nm absorbance with a plate reader. A calibration curve was plotted using the results with the standard specimen, and the oxidized LDL content was determined using the curve.

EXAMPLE 1

Eighteen parts of polysulfone (Udel P-3500 supplied by Teijin Amoco Engineering Plastics Limited) and 9 parts of polyvinylpyrrolidone (Kollidon 30 supplied by BASF) were added to 73 parts of N,N-dimethylacetamide, and heated at 90° C. for 14 hours to ensure dissolution.

This feedstock for membrane production was discharged from an orifice type double-annular nozzle with an outer diameter of 0.3 mm and inner diameter of 0.2 mm while a solution comprising 58 parts of dimethylacetamide and 42 parts of water is used as core liquid. The resultant material was passed through a dry process, and introduced to a 100% water solidification bath to produce a hollow fiber membrane.

The hollow fiber membrane obtained was then put in a 1 wt % polyethyleneimine (supplied by Wako Pure Chemical Industries, Ltd., molecular weight 70,000) solution and irradiated with gamma ray. The gamma ray absorbed dose was 28 kGy. The hollow fiber membrane was in an insoluble state. The number of blood platelets adsorbed by the hollow fiber membrane is shown in Table 1. The oxidized LDL removal rate for the hydrophilic substance used in Example 1 was 24%.

EXAMPLE 2

A hollow fiber membranes produced by the same procedure as in Example 1 was put in a 1 wt % polyethyleneimine (Aldrich reagent, molecular weight 600) solution and irradiated with gamma ray. The gamma ray absorbed dose was 29 kGy. The number of blood platelets adsorbed by the hollow fiber membrane is shown in Table 1.

EXAMPLE 3

A hollow fiber membranes produced by the same procedure as in Example 1 was put in a 1 wt % diethylaminoethyl dextrane (supplied by Sigma, molecular weight 500,000) solution and irradiated with gamma ray. The gamma ray absorbed dose was 29 kGy. The number of blood platelets adsorbed by the hollow fiber membrane is shown in Table 1.

COMPARATIVE EXAMPLE 1

A hollow fiber membranes produced by the same procedure as in Example 1 was put in water and irradiated with gamma ray. The gamma ray absorbed dose was 29 kGy. The number of blood platelets adsorbed by the hollow fiber membrane is shown in Table 1. The oxidized LDL removal rate for the material used in the present Comparative Example 1 was 10%.

COMPARATIVE EXAMPLE 2

A hollow fiber membranes produced by the same procedure as in Example 1 was put in a 0.2 wt % polyvinylpyrrolidone (Kollidon 90 with molecular weight of 1,200,000 supplied by BASF) solution and irradiated with gamma ray. The gamma ray absorbed dose was 29 kGy. The number of blood platelets adsorbed by the hollow fiber membrane is shown in Table 1.

COMPARATIVE EXAMPLE 3

A hollow fiber membranes produced by the same procedure as in Example 1 was put in a 0.2 wt % polyethylene glycol (supplied by Wako Pure Chemical Industries, Ltd., molecular weight 70,000) solution and irradiated with gamma ray. The gamma ray absorbed dose was 29 kGy. The number of blood platelets adsorbed by the hollow fiber membrane is shown in Table 1.

Preparation of Polysulfone Film 1

Ten parts of polysulfone (Udel P-3500 supplied by Teijin Amoco Engineering Plastics Limited) and 0.5 part of polyvinylpyrrolidone (Kollidon 90 supplied by BASF) were added to 89.5 parts of N,N-dimethylacetamide, and dissolved at room temperature to provide feedstock for membrane production. It was cast on a glass plate, heated on a hot plate up to a surface temperature of 100° C., into a layer with a thickness of 203 μm. The surface temperature was measured with a contact-type thermometer. After being cast, the material held on the glass plate was left to stand on the hot plate for five minutes to evaporate the solvent, and immersed in a water bath to produce polysulfone film 1. (Immersion in a water bath aims to allow the film to be peeled easily from the glass plate.)

Preparation of Polysulfone Film 2

Ten parts of polysulfone (Udel P-3500 supplied by Teijin Amoco Engineering Plastics Limited) was added to 90 parts of N,N-dimethylacetamide, and dissolved at room temperature to provide feedstock for membrane production. It was cast by the same procedure as in the case of polysulfone film 1 to produce polysulfone film 2.

EXAMPLE 4

Polysulfone film 1 was put in a 0.1 wt % polyethyleneimine (supplied by Sigma, molecular weight 750,000) solution and irradiated with gamma ray. The gamma ray absorbed dose was 29 kGy. The film was in an insoluble state. The film was then rinsed with purified water, stirred in 80° C. purified water for 60 min, and after replacing the purified water, stirred at 80° C. for another 60 min. The purified water was replaced again and stirring was performed at 80° C. for another 60 min to ensure complete removal of adsorbed polyethyleneimide. The number of blood platelets adsorbed by the film is shown in Table 1.

COMPARATIVE EXAMPLE 4

Polysulfone film 1 was put in a 0.1 wt % polyvinylpyrrolidone (Kollidon K90 supplied by BASF) solution and irradiated with gamma ray. The gamma ray absorbed dose was 27 kGy. The film was in an insoluble state. The film was then rinsed with purified water, stirred in 80° C. purified water for 60 min, and after replacing the purified water, stirred at 80° C. for another 60 min. The purified water was replaced again and stirring was performed at 80° C. for another 60 min to ensure complete removal of adsorbed polyvinylpyrrolidone. The number of blood platelets adsorbed by the film is shown in Table 1.

COMPARATIVE EXAMPLE 5

Polysulfone film 1 was put in a 0.1 wt % polyethylene glycol (supplied by Wako Pure Chemical Industries, Ltd., molecular weight 2,000,000) solution and irradiated with gamma ray. The gamma ray absorbed dose was 28 kGy. The film was then rinsed with purified water, stirred in 80° C. purified water for 60 min, and after replacing the purified water, stirred at 80° C. for another 60 min. The purified water was replaced again and stirring was performed at 80° C. for another 60 min to ensure complete removal of adsorbed polyethylene glycol. The number of blood platelets adsorbed by the film is shown in Table 1.

COMPARATIVE EXAMPLE 6

Polysulfone film 1 was put in water and irradiated with gamma ray. The gamma ray absorbed dose was 28 kGy. The film was then rinsed with purified water, stirred in 80° C. purified water for 60 min, and after replacing the purified water, stirred at 80° C. for another 60 min. The purified water was replaced again and stirring was performed at 80° C. for another 60 min. The number of blood platelets adsorbed by the film is shown in Table 1.

COMPARATIVE EXAMPLE 7

Polysulfone film 2 was put in a 0.1 wt % polyethyleneimine (supplied by Sigma, molecular weight 750,000) solution and irradiated with gamma ray. The gamma ray absorbed dose was 28 kGy. The film was then rinsed with purified water, stirred in 80° C. purified water for 60 min, and after replacing the purified water, stirred at 80° C. for another 60 min. The purified water was replaced again and stirring was performed at 80° C. for another 60 min to ensure complete removal of adsorbed polyethyleneimine. The number of blood platelets adsorbed by the film is shown in Table 1.

COMPARATIVE EXAMPLE 8

Polysulfone film 2 was put in a 0.1 wt % polyvinylpyrrolidone (Kollidon 90 supplied by BASF) solution and irradiated with gamma ray. The gamma ray absorbed dose was 28 kGy. The film was then rinsed with purified water, stirred in 80° C. purified water for 60 min, and after replacing the purified water, stirred at 80° C. for another 60 min. The purified water was replaced again and stirring was performed at 80° C. for another 60 min to ensure complete removal of adsorbed polyvinylpyrrolidone. The number of blood platelets adsorbed by the film is shown in Table 1.

COMPARATIVE EXAMPLE 9

Polysulfone film 2 was put in a 0.1 wt % polyethylene glycol (supplied by Wako Pure Chemical Industries, Ltd., molecular weight 2,000,000) solution and irradiated with gamma ray. The gamma ray absorbed dose was 27 kGy. The film was then rinsed with purified water, stirred in 80° C. purified water for 60 min, and after replacing the purified water, stirred at 80° C. for another 60 min. The purified water was replaced again and stirring was performed at 80° C. for another 60 min to ensure complete removal of adsorbed polyethylene glycol. The number of blood platelets adsorbed by the film is shown in Table 1.

COMPARATIVE EXAMPLE 10

Polysulfone film 2 was put in water and irradiated with gamma ray. The gamma ray absorbed dose was 27 kGy. The film was then rinsed with purified water, stirred in 80° C. purified water for 60 min, and after replacing the purified water, stirred at 80° C. for another 60 min. The purified water was replaced again and stirring was performed at 80° C. for another 60. The number of blood platelets adsorbed by the film is shown in Table 1.

TABLE 1

| | | Membrane component in feedstock | | Polymer in solution | | Number of platelets |
|---|---|---|---|---|---|---|
| | Form | Type | wt % | Type (molecular weight) | wt % | |
| Example 1 | Hollow fiber membrane | PSf/PVP | 18/9 | Polyethyleneimine (70,000) | 1 | 8.7 |
| Example 2 | Hollow fiber membrane | PSf/PVP | 18/9 | Polyethyleneimine (600) | 1 | 6.3 |
| Example 3 | Hollow fiber membrane | PSf/PVP | 18/9 | Diethylaminoethyl dextran (500,000) | 1 | 18.7 |
| Comparative example 1 | Hollow fiber membrane | PSf/PVP | 18/9 | None | — | 55.7 |
| Comparative example 2 | Hollow fiber membrane | PSf/PVP | 18/9 | PVP (1,200,000) | 0.2 | 47.5 |
| Comparative example 3 | Hollow fiber membrane | PSf/PVP | 18/9 | Polyethylene glycol (20,000) | 0.2 | 30.4 |
| Example 4 | Film | PSf/PVP | 10/0.5 | Polyethyleneimine (750,000) | 0.1 | 4.3 |
| Comparative example 4 | Film | PSf/PVP | 10/0.5 | PVP (1,200,000) | 0.1 | 18 |
| Comparative example 5 | Film | PSf/PVP | 10/0.5 | Polyethylene glycol (2,000,000) | 0.1 | 24.7 |
| Comparative example 6 | Film | PSf/PVP | 10/0.5 | None | — | 56 |
| Comparative example 7 | Film | PSf | 10 | Polyethyleneimine (750,000) | 0.1 | 64 |
| Comparative example 8 | Film | PSf | 10 | PVP (1,200,000) | 0.1 | 54.5 |
| Comparative example 9 | Film | PSf | 10 | Polyethylene glycol (2,000,000) | 0.1 | 53 |
| Comparative example 10 | Film | PSf | 10 | None | — | 74.7 |

PSf: polysulfone
PVP: polyvinylpyrrolidone

From Table 1, it is seen that the number of adsorbed blood platelets is small in Examples, while the number is large in Comparative example 1 where cationic polymers were not used and Comparative examples 2 and 3 where polyvinylpyrrolidone and polyethylene glycol, which are neutral, are used respectively.

INDUSTRIAL APPLICABILITY

The hydrophilic substance production method of the present invention can be used for such applications as blood purification, and can provide materials particularly high in compatibility with blood, indicating that it is extremely useful.

The invention claimed is:

1. A method of adsorbing lipid peroxide from blood comprising contacting blood with a hydrophilic substance resistant to absorption of blood platelets and comprising a polyvinylpyrrolidone-containing material and a polyethyleneimine, both of which are in a water-insoluble state.

2. The method according to claim 1 wherein said polyvinylpyrrolidone-containing material contains both polyvinylpyrrolidone and a polysulfone-based polymer.

3. The method according to claim 1 wherein the hydrophilic substance is in the form of a hollow fiber membrane.

4. The method according to claim 1 wherein the hydrophilic substance is a separation membrane for artificial kidneys.

5. A method of adsorbing lipid peroxide from blood comprising contacting blood with a hydrophilic substance resistant to absorption of blood platelets and comprising a polyvinylpyrrolidone-containing material and a polyethyleneimine, both of which are in a water-insoluble state, wherein adhesiveness to blood platelets of the hydrophilic substance is 8.7 platelets/$1.0 \times 10^3$ $\mu m^2$ or less.

6. The method according to claim 5 wherein said polyvinylpyrrolidone-containing material contains both polyvinylpyrrolidone and a polysulfone-based polymer.

7. The method according to claim 5 wherein the hydrophilic substance is in the form of a hollow fiber membrane.

8. The method according to claim 5 wherein the hydrophilic substance is a separation membrane for artificial kidneys.

* * * * *